(12) United States Patent
Laukkanen

(10) Patent No.: US 10,687,773 B2
(45) Date of Patent: Jun. 23, 2020

(54) MAMMOGRAPHY APPARATUS

(71) Applicant: PLANMED OY, Helsinki (FI)

(72) Inventor: Tapio Laukkanen, Espoo (FI)

(73) Assignee: Planmeca OY, Helsinki (FI)

( * ) Notice: Subject to any disclaimer, the term of this patent is extended or adjusted under 35 U.S.C. 154(b) by 40 days.

(21) Appl. No.: 15/039,789

(22) PCT Filed: Dec. 1, 2014

(86) PCT No.: PCT/FI2014/050935
§ 371 (c)(1),
(2) Date: May 26, 2016

(87) PCT Pub. No.: WO2015/079119
PCT Pub. Date: Jun. 4, 2015

(65) Prior Publication Data
US 2017/0020471 A1  Jan. 26, 2017

(30) Foreign Application Priority Data

Nov. 29, 2013  (FI) ..................................... 20130360

(51) Int. Cl.
*A61B 6/00* (2006.01)

(52) U.S. Cl.
CPC ............ *A61B 6/462* (2013.01); *A61B 6/4464* (2013.01); *A61B 6/467* (2013.01); *A61B 6/502* (2013.01)

(58) Field of Classification Search
CPC ....... A61B 6/462; A61B 6/502; A61B 6/4464; A61B 6/467
See application file for complete search history.

(56) References Cited

U.S. PATENT DOCUMENTS

| 4,674,107 | A | 6/1987 | Urban et al. | |
|---|---|---|---|---|
| 5,572,565 | A * | 11/1996 | Abdel-Mottaleb | ... G06T 7/0012 378/37 |
| 7,496,398 | B2 * | 2/2009 | Nields | .................. A61B 6/0435 378/37 |
| 2003/0073895 | A1 | 4/2003 | Nields et al. | |
| 2003/0091150 | A1 * | 5/2003 | Barber | .................. A61B 6/107 378/189 |
| 2003/0212327 | A1 * | 11/2003 | Wang | ..................... A61B 6/463 600/437 |
| 2003/0233040 | A1 | 12/2003 | Sakaniwa | |
| 2004/0218352 | A1 * | 11/2004 | Hillman | ................. F16M 11/10 361/679.06 |

(Continued)

FOREIGN PATENT DOCUMENTS

| CN | 102648854 A | 8/2012 |
|---|---|---|
| CN | 102429678 B | 8/2016 |

(Continued)

*Primary Examiner* — Chih-Cheng Kao
(74) *Attorney, Agent, or Firm* — Fay Sharpe LLP

(57) ABSTRACT

The invention relates to mammography apparatuses, especially to the user interfaces of mammography apparatuses. A mammography apparatus according to the invention comprises a certain basic structure and a user interface arrangement placed to this basic structure, the user interface arrangement being implemented to enable aligning of the view of the user interface both such that the view is only visible to the operator of the apparatus and such that a patient positioned for imaging can see it.

20 Claims, 4 Drawing Sheets

(56) References Cited

U.S. PATENT DOCUMENTS

Figure 1:
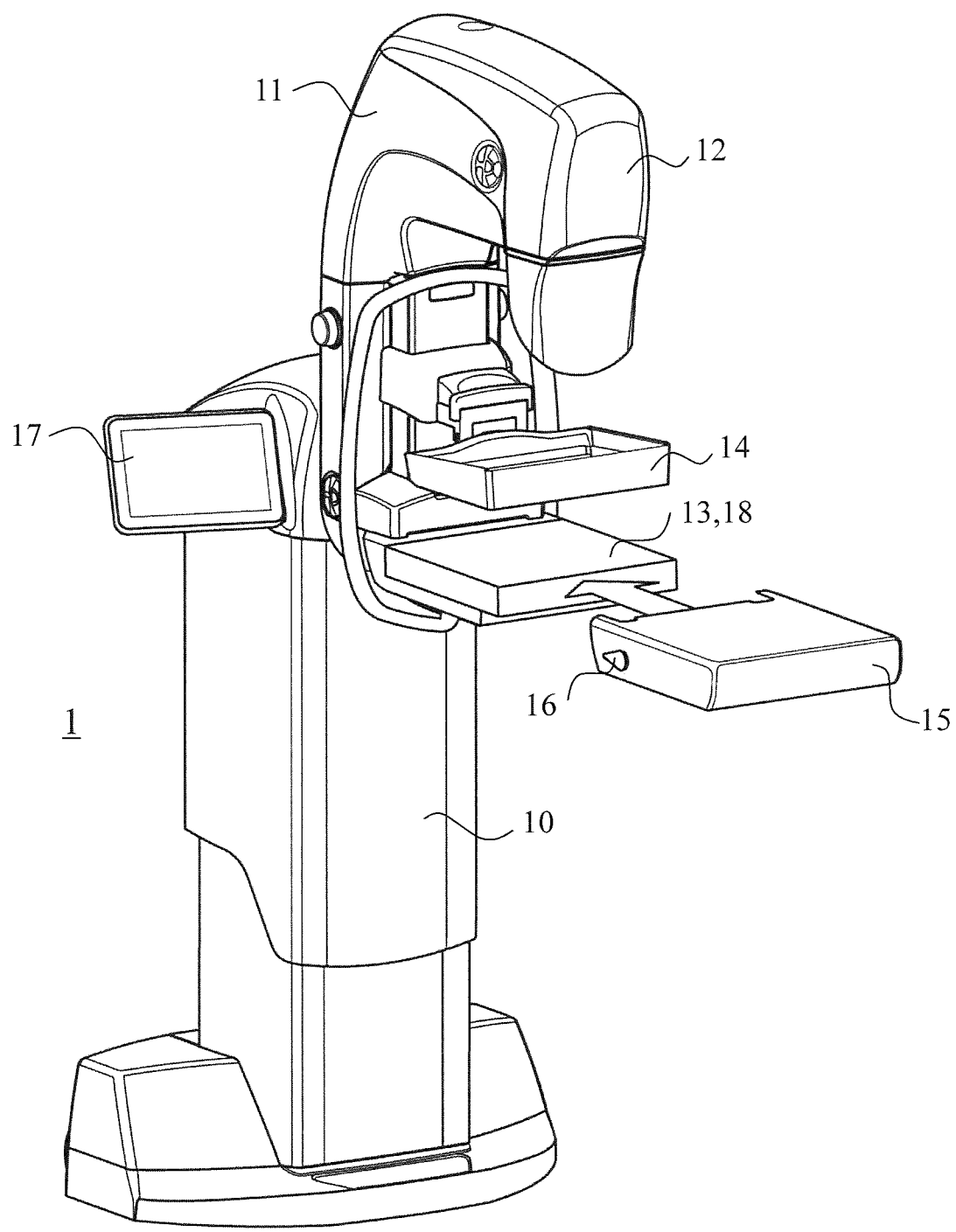

| | | | | |
|---|---|---|---|---|
| 2004/0264635 | A1* | 12/2004 | Eberhard | A61B 6/025 378/22 |
| 2005/0234327 | A1* | 10/2005 | Saracen | A61B 6/0457 600/407 |
| 2007/0036265 | A1* | 2/2007 | Jing | A61B 6/025 378/37 |
| 2007/0274438 | A1* | 11/2007 | Hyvarinen | A61B 6/0414 378/37 |
| 2008/0009696 | A1* | 1/2008 | Hempel | A61B 5/055 600/407 |
| 2008/0087830 | A1 | 4/2008 | Kashiwagi | |
| 2008/0095420 | A1 | 4/2008 | Ohyu et al. | |
| 2011/0286575 | A1 | 11/2011 | Omernick et al. | |
| 2012/0016222 | A1* | 1/2012 | Bouvier | A61B 6/102 600/407 |
| 2012/0053455 | A1* | 3/2012 | Okada | A61B 6/00 378/98.5 |
| 2012/0093298 | A1 | 4/2012 | Lalena | |
| 2012/0317724 | A1* | 12/2012 | Buettner | A61B 6/03 5/601 |
| 2016/0051067 | A1* | 2/2016 | Law | F16M 11/041 361/679.22 |
| 2016/0151032 | A1* | 6/2016 | Muller | A61B 6/0414 378/37 |

FOREIGN PATENT DOCUMENTS

| | | |
|---|---|---|
| DE | 102010011663 A1 | 9/2010 |
| DE | 10 2010 011663 A1 | 9/2011 |
| JP | 2009077969 A | 4/2009 |
| WO | 2015/008117 A1 | 1/2015 |
| WO | 2015008117 A1 | 1/2015 |

* cited by examiner

MAMMOGRAPHY APPARATUS

FIELD OF THE INVENTION

The present invention relates to mammography apparatuses, especially to the user interfaces of mammography apparatuses.

DESCRIPTION OF PRIOR ART

Breast cancer is the most common type of cancer in women. According to investigations, about one in every ten women contracts breast cancer at some point in their lives. When breast cancer is detected on the basis of symptoms, the illness often has already developed to a stage where the prognosis for recovery is relatively poor. Some of the cases are detected in screening programs arranged in many countries for women over the age of 40. Screening often meals a cancer at a very early stage, so its treatment can be started in time and recovery is thus more likely.

Mammography is a widely used method in breast cancer screening as a clinical investigation method and also in follow-up diagnosis. Mammography is an X-ray imaging method wherein an apparatus specifically designed for this purpose is used. In screening studies, mammography has been reported to have a sensitivity of 90-93% and a specificity of 90-97%. This indicates that screening studies are useful and that early detection of breast cancer by screening can save human lives. It has been established that mammography reduces breast cancer mortality by 35 percent among women over 50 and by 25-35 percent among women at the age of 40-50 years.

The mammography images are examined to detect various anomalies in the breast, such as calcifications, i.e. small deposits of calcium in the soft breast tissue. A calcification generally cannot be detected by feeling the breast, but it is visible in the x-ray image. Large calcifications are generally not associated with cancer, but clusters of small calcium deposits, i.e. so-called micro-calcifications, are an indication of extra breast cell activity, which may be associated with breast cancer. Other features to be detected by mammography include cysts and fibroadenomas, which, however, are generally not associated with cancer.

In conventional screening mammography, the breast gland is typically compressed between two compression plates and exposed to radiation at least twice, from above and from an oblique direction. If necessary, an additional third image is taken squarely from the side. As in such imaging the tissue layers lie on top of each other in the direction of the x-ray beam, these irradiations produce two-dimensional images in which strongly absorbing structures may hinder the detection of structures lying beneath them.

Continual improvement in mammography has led to novel type of mammography methods and devices that produce tomographic images of a patient's breast. In these solutions, several projections of the breast at different angles are produced and an image is generated by using an applicable reconstruction algorithm. From the image information, i.e. from the individual images, typically several images are constructed which represent layers of the breast oriented in parallel with the surface of the x-ray detector, thus making possible to detect tissue structures laying on top of each other.

A typical digital mammography apparatus comprises a frame part and a C-arm or a corresponding structure rotatably connected to the frame part. At the first end of the C-arm, there is arranged an x-ray source and at the second end, a radiation detector. A term imaging means is often used for these devices. Disposed substantially in the region between said x-ray source and detector, typically at a close proximity to the detector, a compression structure is arranged which is designed to position a breast as compressed for the duration of an exposure.

Mammography patients often experience varying degrees of anxiety that may be related not only to the general fear regarding a possible disease the examination may discover as such but also, for example, to the fear of physical pain the compressing of a breast for the imaging process or the injecting of a biopsy needle into the breast tissue may cause. As the patient's anxiety may affect the patient's behavior, and thus the success of the imaging or sampling, all means by which the patient's fears can be alleviated are welcomed.

User interfaces of the mammography apparatus are traditionally fixed structures and as the name suggests, specifically designed to be seen and used by the user of the apparatus. Such solutions do not actually have a function considering alleviating the patient's fears.

SUMMARY OF THE INVENTION

The object of the present invention and its preferable embodiments is to accomplish a new kind of mammography apparatus including integrated structures thanks to which it is possible, for example, to alleviate the patient's fears or to deliver information to the patient of an upcoming operation or during an operation. This is due to the invention offering new kinds of possibilities for delivering information to the patients.

The object of the invention is achieved by a solution of the accompanying independent claim. Some preferable embodiments of the invention have been presented in the accompanying dependent claims.

The invention and its preferable embodiments provide a new kind of way to guide and calm the patient or to provide information during mammography imaging or biopsy procedures.

DETAILED DESCRIPTION OF THE INVENTION

Figure 2A:
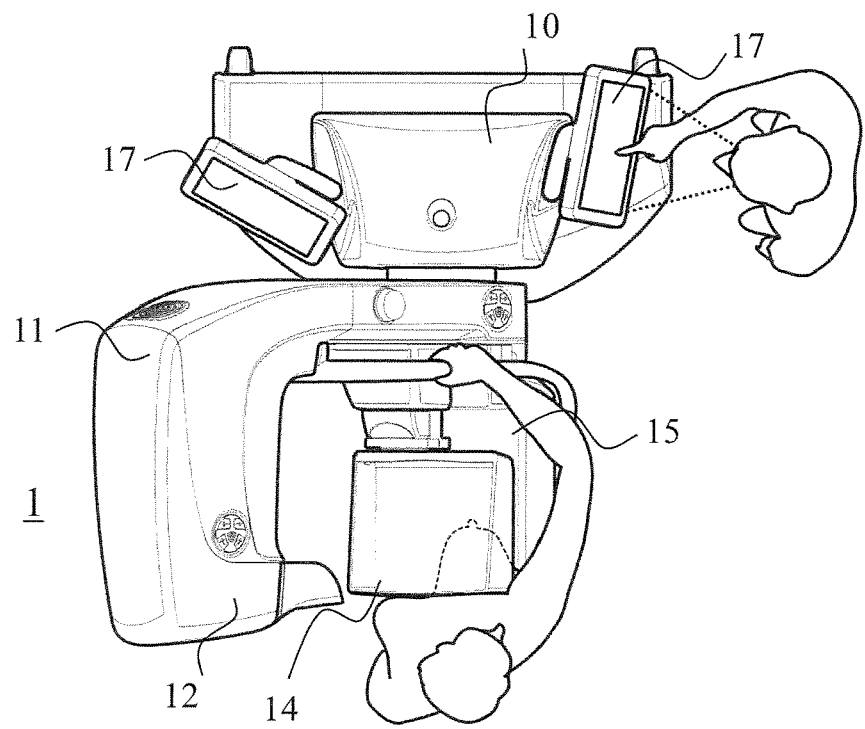
Figure 2B:
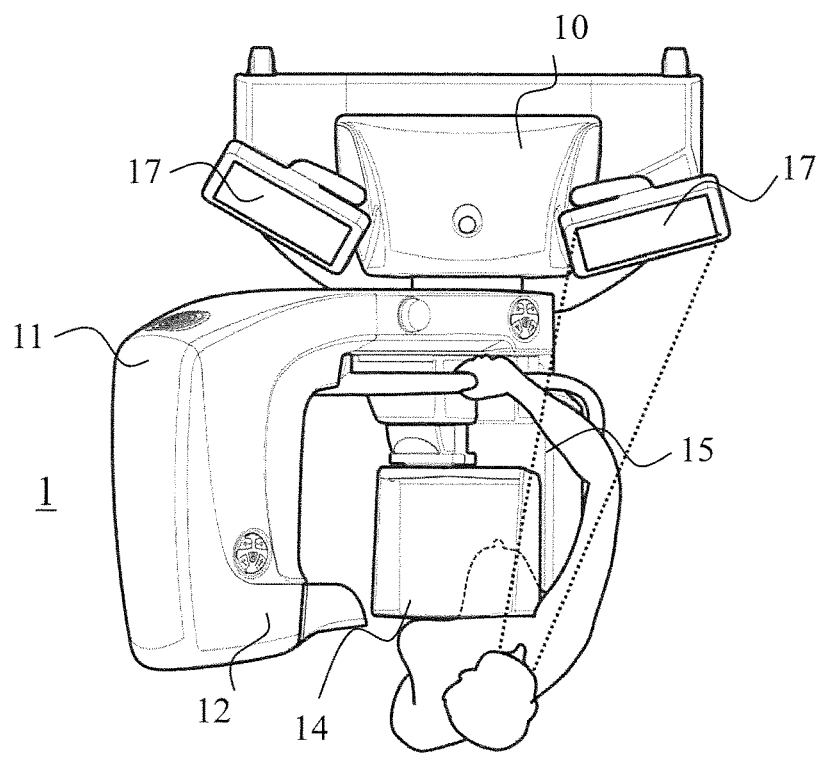
Figure 2C:
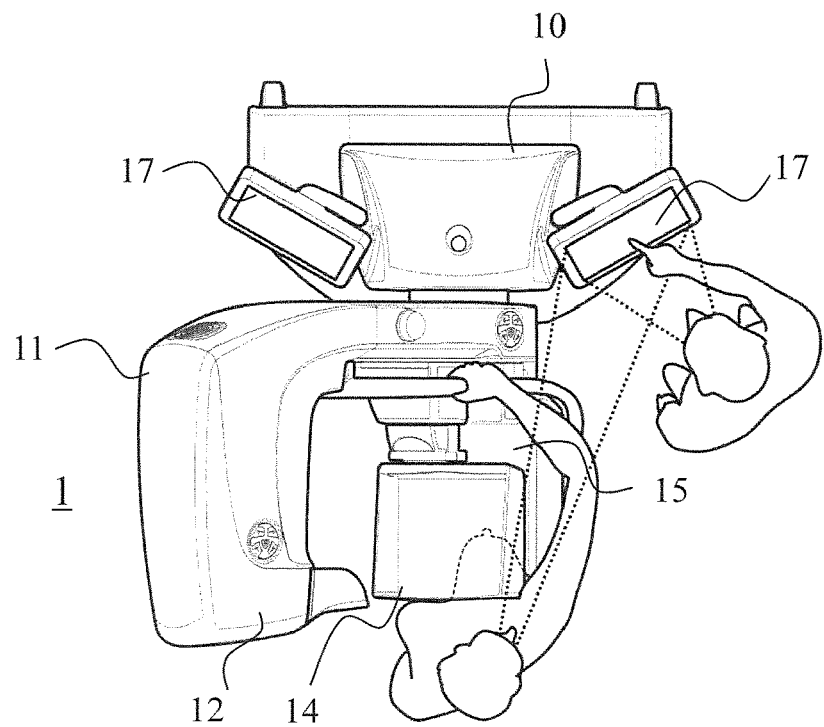
Figure 3:
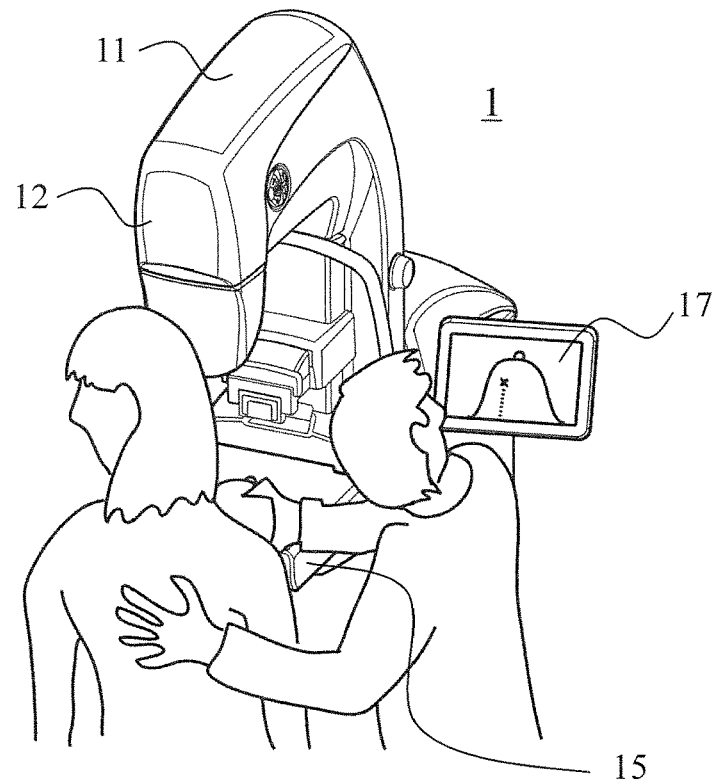
Figure 4:
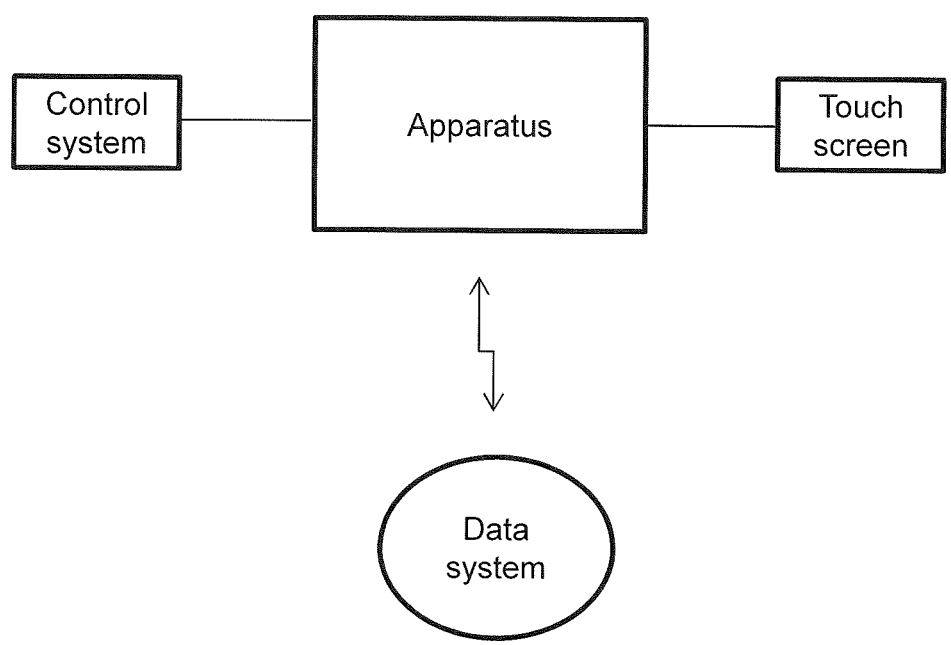

In the following, some embodiments of the invention and their benefits will be described in more detail, also with help of the attached figures, of which figures FIG. 1 shows a structure of one mammography apparatus according to the invention, FIGS. 2a, 2b and 2c show a mammography apparatus according to FIG. 1 in an oblique imaging position and as viewed from above, FIG. 3 shows a solution in which information which facilitates patient positioning is being presented on a screen connected to a mammography apparatus and FIG. 4 is a diagrammatic presentation of an arrangement for presenting information in connection with a mammography imaging apparatus.

DETAILED DESCRIPTION OP THE INVENTION

A mammography apparatus (1) presented in FIG. 1 consists of a substantially vertically standing frame part (10) and an arm structure (11) connected to it. An X-ray source (12) is arranged to the upper part of the arm structure (11), within its cover, the x-ray source (12) being arranged to generate a beam which goes through an upper compression plate (14) of the mammography apparatus (when such upper compression plate is connected to the apparatus) and towards a detector (18) placed in a detector housing (13). The detector housing (13) or a corresponding structure is typically arranged inside a lower tray structure (15). The lower tray structure (15) can be a structure fixed to the apparatus or it can be arranged as removably connected. When the upper surface of the lower tray structure (15) typically functions as a platform on which a breast is positioned for imaging, this structure is often also referred to as a lower compression plate. In the solution according to FIG. 1, attaching means (16) is arranged to the lower tray structure (15) to enable its releasable connection to the mammography apparatus (1). In addition, a screen (17) belonging to the user interface of the apparatus, to be described in more detail below, is arranged to the apparatus according to FIG. 1.

FIGS. 2*a*-2*c* show the apparatus according to FIG. 1 as viewed from above and in an oblique imaging position. Two touch screens (17) are arranged to the frame part (10) of the apparatus, on the opposite sides of the frame part (10). Attachment of the touch screen (17) to the frame part (10) of the apparatus is articulated such that the touch screen (17) can be turned at least to both a first position in which it is aligned away from the lower tray structure (15) of the apparatus (FIG. 2*a*), in connection with which structure the patient is positioned for imaging or operations, and to a second position (FIG. 2*b*) in which it is at least partly aligned towards said lower tray structure (15), i.e. it is in such position that the patient has a line of sight to the screen (17).

A position is presented in FIG. 3 intermediate to the previous positions which is applicable for consultation, for example, in which position both the operator of the apparatus and the patient have a good view at the screen (17).

The first position of the touch screen (17) according to FIG. 2*a* can be used when operations of the apparatus are controlled or when information is presented on the touch screen which one does not want the patient to see or which the patient needs no to see. Also the position according to FIG. 2*b*, and especially according to FIG. 2C can be used when controlling operation of the apparatus, but those positions of the touch screen (17) are especially designed to be used for delivering information to the patient.

In reference to FIG. 4, according to one preferable embodiment of the invention, the touch screen (17) is arranged in functional connection with the control system of the apparatus to display imaging parameter values, for example, or the time remaining in the imaging process. Information can be delivered on the display e.g. an when exactly the exposure will start and the patient should remain still or how Long the operation in progress will still last. This kind of functional connection can also be arranged e.g. to a patient data base, whereby one preferable embodiment according to the invention includes a solution in which a touch screen (17) is arranged in a functional connection with an information system in which images of a patient taken earlier have been recorded. It is known as such to use information achievable from such images to facilitate patient positioning when the same object is being re-imaged or when a biopsy is to be started or is going on, which information may include measurement markings or other made to the images relating to findings which have been detected. According to prior art, though, such images taken earlier have been studied at some separate workstation, but the present invention makes it possible to bring the images to the immediate vicinity of the place where that information is needed. Then, the arrangement preferably includes a possibility to present images of a patient's breast taken earlier and especially in the same orientation in which the breast is being positioned to the imaging apparatus, in which images, as said, measurement markings or other may have been made relating to findings which have been detected. FIG. 3 demonstrates a situation like this.

When a touch screen being in functional connection with appropriate system is arranged in connection with an imaging station of a mammography apparatus it will be possible not only to alter characteristics of an earlier image of the breast being the target of an operation but also e.g. to make measurement markings on the image in connection with a new positioning of the breast for some operation.

Guiding and informing of the patient of various stages of an imaging or biopsy event can help in achieving a successful procedure, by e.g. helping the patient to be still throughout an operation which may take quite a while.

The touch screen solution according to the invention can also be realized to allow for the patient herself to control operation of the mammography apparatus when the patient's breast is being compressed for imaging. Such solution is prone to lessen the fears of the patient relating to compressing a breast, taking in consideration that there are studies according to which a patient may allow the mammography apparatus to compress a breast even more when she can control the compressing process herself. The solution according to the invention may thus offer the possibility to bring a touch screen (17) arranged to control operation of the mammography apparatus so close to the lower tray structure (15) of the apparatus that the patient can herself control via it e.g. movements of the upper compression plate (14) of the apparatus according to FIG. 1.

In one embodiment of the invention the articulation of the touch screen (17) is realized as motorized. Then, at least one operation mode can be arranged to the control system of the apparatus according to which the touch screen (17) automatically turns into a position which has been designated for it in that operation mode. The position of the touch screen (17) can thus be arranged to be changed according to which procedure that operation mode relates to, or according to what the control system displays on the screen. The touch screen (17) can be arranged e.g. to turn towards the patient e.g. when the time remaining in the imaging process is displayed on the screen. On the other hand, also in the came of an articulation being implemented to be turned manually, one or more views may be defined in the control system which are automatically displayed on the touch screen (17) when it is turned into a position in which it comes to the field of view of the patient, i.e. into a position as aligned towards the lower tray structure (15).

The orientation of the view presented on the screen can be implemented instead of articulated, e.g. by arranging a sliding or rotating polarizing film or some other similar application on top of the screen.

The screen used in the apparatus can at its simplest be just a screen, but preferably it is either a real and traditional touch screen or some other user interface with a screen.

This mammography apparatus according to the invention and its preferable embodiments thus include apparatus equipped with a control system and including a substantially vertically standing frame part (10) or a frame part (10) attachable to a wall or a ceiling, an arm structure (11) connecting to this frame part (10) and pivotable in relation to a horizontal rotation axis, at a substantially first end of the opposite ends of the arm structure (11) is placed an X-ray source (12), and substantially at a second end an image data receiving means (18), and in connection with said second end of the arm structure (11) is additionally arranged a lower tray structure (15) positioned substantially on top of the image data receiving means (18). The user interface arrangement of the apparatus includes at least on screen (17) or at least one touch screen (17) or equivalent which is attached to the frame part (10) of the apparatus as articulated or implemented with a technology by which the direction from which information presented on the screen is visible is adjustable. Regardless of the structure used it is implemented such that the view of the screen (17) or touch screen (17) can be pointed to at least two different directions out of which in the first the view is directed away from the lower tray structure (15) and in the other at least partly towards the lower tray structure (15).

Preferably the frame part (10) of the apparatus includes a vertically extending floor attached construction and screens (17) or touch screens (17) being arranged at least one on both sides of the frame part (10), as viewed from the lower tray structure. The articulation of the screen can be implemented as motorized and the control system of the apparatus can include at least one operation mode according to which the screen (17) or the touch screen (17) automatically turns into a position determined for it by said operation mode, as dependent on the operation to which the operation mode relates to or on what the control system shows' on the screen (17) or the touch screen (17). Defined in the control system there may also be one or several views which are to be automatically presented on the display (17) or on the touch screen (17) when it is turned to some specific position, especially to a position in which it is at least partly facing the lower tray structure of the apparatus, i.e. such position that the person positioned for imaging in the apparatus has a line of sight to the screen. The articulation to the apparatus can also be implemented such that the screen (17) or touch screen (17) can be brought to the substantial vicinity of the lower tray structure (15), especially at an arm's length or closer. Further, the apparatus can be arranged with means for bringing it into a functional connection with an information system in which images taken of a patient are recorded, as well as with means for presenting images recorded in the information system on a screen (17) or a touch screen (17). Preferably these means for presenting images include means for presenting said images in an orientation which corresponding to the orientation in which the breast is being positioned for imaging or some other operation on top of said lower tray structure (15).

The invention claimed is:
1. A mammography apparatus, which includes
a substantially vertically standing frame part or a frame part attachable to a wall or a ceiling,
an arm structure connecting to said frame part and pivotable in relation to a horizontal rotation axis,
wherein at a substantially first end of the opposite ends of the arm structure is placed an X-ray source and substantially at a second end an image data receiving means, and
wherein in connection with said second end of the arm structure is additionally arranged a lower tray structure, positioned substantially on top of the image data receiving means and
a control system and in connection with it a user interface arrangement, said user interface arrangement being attached to the frame, characterized in that said user interface arrangement includes at least one display or at least one touch screen, which is

(i) attached as articulated to the frame part such that a view of said at least one display or touch screen can be aligned in at least two directions or
(ii) implemented with a technology by which a direction in which information on the display is visible is adjustable so that a view of said at least one display or touch screen can be aligned in at least two directions,
and wherein in both embodiment (i) and (ii) there is a first direction in which the view is aligned away from said lower tray structure so that a patient when positioned at the lower tray structure and her eyes facing the display or touch screen does not have a line of sight to information on the display or touch screen and a second direction which is aligned at least partially towards said lower tray structure so that the patient when positioned at the lower tray structure and her eyes facing the display or touch screen has a line of sight to the display or touch screen and can view the information.

2. Mammography apparatus according to claim 1, characterized in that the frame part of the apparatus comprises a vertically extending structure mountable on a floor and said displays or touch screens are arranged thereto at least one on each side of the frame part, as viewed from said lower tray structure.

3. Mammography apparatus according to claim 1, characterized in that said at least one display or touch screen is attached to the frame part as articulated, the articulation being realized as motorized, and said control system comprises at least one operation mode according to which the display or the touch screen automatically turns into a position determined for it by said operation mode, as dependent on the operation to which the operation mode relates to, or on what the control system shows on the display or touch screen.

4. Mammography apparatus according to claim 1, characterized in that one or several views have been defined in the control system to be automatically presented on the display or on the touch screen when it is aligned in said second direction.

5. Mammography apparatus according to claim 1, characterized in that said control system comprises at least one touch screen attached to the frame part as articulated, the articulation being realized so that the touch screen can be brought to within the patients arm length or closer.

6. Mammography apparatus according to claim 5, wherein the user interface arrangement includes at least one touch screen and said touch screen provides a function allowing a patient to control operation of the apparatus while said patient is being imaged or while said patient is positioning a breast for imaging.

7. Mammography apparatus of claim 6, wherein the patient controls a compressing of the breast via the display or touch screen.

8. Mammography apparatus according to claim 1, characterized in that the apparatus includes means arranged to bring the apparatus into a functional connection with an information system in which patient images are recorded, and a means to show said patient images recorded in the information system on said display or touch screen.

9. Mammography apparatus according to claim 8, characterized in that said means for showing images includes a means for presenting said images in an orientation corresponding to an orientation in which a breast is being positioned on top of said lower tray structure.

10. Mammography apparatus according to claim 1, wherein the at least one display or touch screen displays time remaining in an imaging process for viewing by a patient being imaged.

11. Mammography apparatus according to claim 1, wherein the at least one display or touch screen includes an intermediate direction in which both a patient being imaged and an operator can simultaneously view a screen for consultation.

12. Mammography apparatus according to claim 1, wherein the user interface arrangement comprises a touch screen through which operation of the apparatus is controlled.

13. Mammography apparatus according to claim 1, wherein an image of a patient's compressed breast is displayed on the user interface arrangement.

14. Mammography apparatus according to claim 1, wherein the image data receiving means and the display or touch screen are secured to separate locations on the frame.

15. Mammography apparatus according to claim 1, including two displays or touch screens on opposed sides of said frame part.

16. Mammography apparatus of claim 1, wherein when the patient is positioned at the lower tray structure and her eyes facing the display or touch screen, her breast is also engaged by the lower tray structure.

17. Mammography apparatus of claim 1, including only one display or touch screen.

18. Mammography apparatus of claim 1, wherein the display or touch screen is implemented with a technology by which a direction in which information on the display is visible is adjustable so that a view of said display or touch screen can be aligned in at least two directions.

19. Mammography apparatus of claim 1, wherein an articulation of the display in said at least two directions is motorized.

20. Mammography apparatus of claim 19, wherein the display is automatically articulated by the control system based on an operation being performed by the apparatus.

* * * * *